United States Patent
Wu et al.

(10) Patent No.: US 11,492,319 B2
(45) Date of Patent: Nov. 8, 2022

(54) PREPARATION AND APPLICATION METHOD OF BIO-BASED LONG-CHAIN ALCOHOL-ETHER OXYGENATE DIESEL ADDITIVES

(71) Applicant: SOUTHEAST UNIVERSITY, Nanjing (CN)

(72) Inventors: Shiliang Wu, Nanjing (CN); Rui Xiao, Nanjing (CN); Yuan Liu, Nanjing (CN); Ziwei Wang, Nanjing (CN)

(73) Assignee: SOUTHEAST UNIVERSITY, Nanjing (CN)

( * ) Notice: Subject to any disclaimer, the term of this patent is extended or adjusted under 35 U.S.C. 154(b) by 86 days.

(21) Appl. No.: 17/289,248

(22) PCT Filed: Sep. 29, 2020

(86) PCT No.: PCT/CN2020/118605
§ 371 (c)(1),
(2) Date: Apr. 28, 2021

(87) PCT Pub. No.: WO2021/129022
PCT Pub. Date: Jul. 1, 2021

(65) Prior Publication Data
US 2022/0106244 A1    Apr. 7, 2022

(30) Foreign Application Priority Data

Dec. 24, 2019   (CN) .......................... 201911351924.5

(51) Int. Cl.
| | |
|---|---|
| *C07C 41/03* | (2006.01) |
| *C10L 1/185* | (2006.01) |
| *C10B 53/02* | (2006.01) |
| *C10B 57/10* | (2006.01) |

(52) U.S. Cl.
CPC .............. *C07C 41/03* (2013.01); *C10B 53/02* (2013.01); *C10B 57/10* (2013.01); *C10L 1/1852* (2013.01); *C10L 2200/0469* (2013.01); *C10L 2270/026* (2013.01); *C10L 2290/02* (2013.01); *C10L 2290/08* (2013.01); *Y02E 50/10* (2013.01)

(58) Field of Classification Search
None
See application file for complete search history.

(56) References Cited

FOREIGN PATENT DOCUMENTS

| CN | 103562353 A | | 2/2014 | |
|---|---|---|---|---|
| CN | 104998640 A | | 10/2015 | |
| CN | 105132003 A | | 12/2015 | |
| CN | 105289423 A | | 2/2016 | |
| CN | 106995733 A | * | 8/2017 | ............. Y02E 50/13 |
| CN | 110093179 A | | 8/2019 | |
| CN | 110099986 A | | 8/2019 | |
| CN | 110964548 A | | 4/2020 | |
| WO | 2019130022 A2 | | 7/2019 | |

* cited by examiner

*Primary Examiner* — Rosalynd A Keys
(74) *Attorney, Agent, or Firm* — Bayramoglu Law Offices LLC

(57) ABSTRACT

A biomass-based long-chain alcohol ether oxygenated additive and a preparation method and application thereof are disclosed. The additive used agricultural and forestry wastes as raw materials, and has a general chemical formula of R—(O—$C_{1-3}$)$_n$—R—OH. The preparation method includes the following steps: step 1, performing drying pretreatment on biomass raw materials, performing rapid pyrolysis under an inert atmosphere to obtain a pyrolysis product containing water, gases, water-phase bio-oil and oil-phase bio-oil, separating out the water-phase bio-oil and performing catalytic hydrogenation on the water-phase bio-oil to obtain polyols; step 2, performing catalytic dehydration on the polyols obtained in step 1 under a basic catalyst system to obtain epoxyalkane; and step 3, making the epoxyalkane obtained in step 2 and methanol undergo a reaction under a molecular sieve catalyst and removing the solid catalyst by separation to obtain the long-chain alcohol ether oxygenated additive.

4 Claims, 4 Drawing Sheets

US 11,492,319 B2

PREPARATION AND APPLICATION METHOD OF BIO-BASED LONG-CHAIN ALCOHOL-ETHER OXYGENATE DIESEL ADDITIVES

CROSS REFERENCE TO THE RELATED APPLICATIONS

This application is the national phase entry of International Application No. PCT/CN2020/118605, filed on Sep. 29, 2020, which is based upon and claims priority to Chinese Patent Application No. 201911351924.5, filed on Dec. 24, 2019, the entire contents of which are incorporated herein by reference.

TECHNICAL FIELD

The present invention relates to alternative fuels and diesel fuel additives, and specifically relates to a biomass-based long-chain alcohol ether oxygenated additive and a preparation method and application.

BACKGROUND

Reserves of agricultural and forestry wastes in China are abundant but are not effectively used, and environmental pollution is produced. A large amount of PM2.5 is emitted due to incomplete combustion of gasoline and diesel in motor vehicles, which also causes environmental pollution. A lot of researches at home and abroad show that PM2.5 emission can be greatly reduced by adding oxygenated liquid fuels into gasoline and diesel. Biomass naturally contains oxygen and is an ideal raw material for preparing oxygenated liquid fuels.

Particulate matter emission of diesel engines with compression ignition diffusion combustion is higher than that of gasoline engines with premixed combustion. At present, the use of oxygenated fuel additives to reduce particulate matter emission of diesel engines has become a mainstream emission reduction way due to further improvement of particulate matter emission standards for internal combustion engines. A local oxygen deficiency phenomenon in a diffusion process of diesel can be avoided by using "self-contained oxygen" of oxygenated additives so that more complete combustion is achieved. Oxygenated additives are mainly classified into alcohol oxygenated additives, ester oxygenated additives and ether oxygenated additives according to functional groups.

Rapid pyrolysis of biomass can convert the biomass, mainly including wastes such as wood chips and straw, into bio-oil which is easy to store and transport and high in energy density by a continuous process in a factory-based production manner, but compositions of the bio-oil are very complicated, physical and chemical properties (high water content, high acidity and high particulate matter content) are unstable. The bio-oil can be converted into additives of diesel or gasoline and other internal combustion engine fuels after further modification and upgrading. At present, mainstream bio-oil upgrading methods include catalytic cracking, catalytic hydrogenation, catalytic esterification and other modification upgrading methods. Unstable oxygenated compounds in the bio-oil are removed, and stable gasoline and diesel products are obtained finally.

In a catalytic cracking process, large molecules of crude oil are cracked into small molecules by using an acidic catalyst under normal pressure without hydrogen supply. Meanwhile, oxygen in the crude oil is removed in the forms of $CO$, $CO_2$, $H_2O$ and so on, so that the oxygen content of the biological crude oil is reduced, and the stability of the bio-oil is improved. Catalytic cracking can be performed under normal pressure without consumption of hydrogen in the process, so that requirements for equipment are reduced. However, there are also many problems that the catalyst has short service life and is likely to coke and lose activity, the upgraded oil is low in quality and yield and H/C is low.

High-quality biofuels can be obtained by catalytic hydrogenation and upgrading of the biological crude oil, but the reaction temperature is generally 300-600° C., and the hydrogen pressure is generally higher than 10 MPa. In addition, the whole operation process flow is complicated, and the equipment cost is high.

Catalytic esterification refers to that an alcohol additive is added into the bio-oil, and carboxyl groups and other components in the bio-oil are converted into ester substances under the role of the catalyst, so that the acidity and corrosiveness of the bio-oil are reduced, and its stability is improved. A catalytic esterification upgrading process can effectively reduce the pH value of the biological crude oil and increase the molecular chain length, but the selectivity of a catalytic esterification reaction is low, other cross-reactions may be caused, and there are also problems of loss and deactivation of the catalyst.

CN105289423A disclosed a method for preparing an oxygenated fuel in a slurry bed of coal synthesis gas. In the invention, swirl movement of a slurry is realized by multiple nozzles, so that bubbles rise in a spiral way, and a stirring function is improved. The time for contacting with the slurry is increased by 1.2-1.8 times, and the temperature difference of the slurry is 4-8° C. According to the invention, the reaction efficiency of a reactor is effectively improved, but additional supply of oxygen is needed due to use of coal raw materials, and thus the production cost is increased.

CN110093179A disclosed a method for preparing a bio-oxygenated fuel by upgrading lignin heavy oil. In the invention, the lignin heavy oil, a reaction medium and a non-precious metal catalyst supported by an alkaline carrier are mixed for reaction under a condition of 1-4 MPa hydrogen pressure at 120-160° C. for 1-5 hours. The catalyst is separated out, the reaction medium is removed, high-efficiency catalytic upgrading of the lignin heavy oil is achieved, and the high-quality bio-oxygenated fuel is obtained. According to the invention, lignin is effectively utilized in a complex treatment means, and the application range is narrow.

CN104998640A disclosed a preparation method and application of Pd—In/C catalyst in preparation of an alcohol oxygenated fuel. The bimetallic catalyst prepared in the invention is applied to a hydrofining reaction of catechol with the highest content of bio-oil phenolic compounds, and catechol can be completely converted into an alcohol oxygenated liquid fuel, but the catalyst of the invention is complicated in preparation means and high in cost, and is not suitable for use in large scale.

According to existing preparation methods of oxygenated fuels, coal and biomass are mainly used as raw materials. The cost is high when coal is used as the raw material, and catalytic cracking, catalytic hydrogenation, catalytic esterification and other methods have different advantages and disadvantages when biomass is used as the raw material. However, target products are mainly short-chain polyols or short-chain esters in the use process mixed with diesel The actual performance of the target products is not good and has problems such as unstable combustion and low mixing ratio. The maximum mixing ratio is 15% and is reduced when the ambient temperature is reduced. Mixing in winter cannot be achieved, and thus popularization and use of biomass-based oxygenated fuels are limited. At the same time, since carbon chains of polyols are much lower than those of diesel, and the combustion characteristics of polyols are greatly different from those of diesel, so polyols cannot be used stably. The currently disclosed preparation methods still stay at using biomass to prepare bio-oil containing hundreds of components, or further upgrading to prepare a specific short-chain component, which has low application value. In addition, a further upgrading process is lacked, thus this type of bio-oil can only be used for low-quality applications such as boiler combustion.

SUMMARY

Objectives of the present invention: In order to overcome the shortcomings in the prior work, one objective of the present invention is to provide a biomass-based long-chain alcohol ether oxygenated additive with high oxygen content, good combustion performance and great emission reduction effect; another objective of the present invention is to provide a preparation method of the biomass-based long-chain alcohol ether oxygenated additive, which is good in economical efficiency, simple to operate, and compatible with current refueling equipment; and a further objective of the present invention is to provide application of the biomass-based long-chain alcohol ether oxygenated additive in liquid fuels, where the additive can be mixed with diesel in any ratio, the use of petroleum resources is reduced, and pollutant emission is reduced.

Technical solution: The biomass-based long-chain alcohol ether oxygenated additive provided by the present invention adopts agricultural and forestry wastes as raw materials, and has a general chemical formula of $R-(O-C_{1-3})_n-R-OH$.

The preparation method of the biomass-based long-chain alcohol ether oxygenated additive includes the following steps:

step 1, Drying pretreatment on biomass raw materials at 100-110° C., weighing the biomass raw materials every 3-6 hours until the mass of biomass is not changed, performing rapid pyrolysis on dried biomass under an inert atmosphere to obtain a pyrolysis product containing water, gases, water-phase bio-oil and oil-phase bio-oil, separating out the water-phase bio-oil, performing catalytic hydrogenation on the water-phase bio-oil, placing the water-phase bio-oil into a reactor, putting 10 wt % of a zeolite catalyst HZSM-5 into the reactor for uniform stirring, introducing hydrogen with a pressure of 3-5 MPa, stirring the mixture at a speed of 20-40 r/min during a reaction at 120-150° C. for 2-2.5 hours, and after the reaction, removing the solid catalyst by separation to obtain polyols;

step 2, performing catalytic dehydration on the polyols obtained in step 1 under a basic catalyst system, where 10 wt % of a basic catalyst is weighed and loaded onto a bed layer, a reactor made of quartz glass is heated to 350-450° C. The temperature is kept unchanged with nitrogen used as a carrier gas, and the polyols are injected into the reactor from an upper part at a rate of 10-100 ml/h by using a liquid injection pump and then enter a catalyst bed layer for a catalytic reaction after gasification. A catalytic product is condensed to obtain epoxyalkane;

step 3, fully and uniformly stirring epoxyalkane obtained in step 2 and methanol according to a molar ratio of 9-12:1 for a reaction at a constant temperature of 60-90° C. for 7-8 hours under a molecular sieve catalyst with a mass fraction of 4-6 wt %, then cooling the mixture to room temperature, and removing the solid catalyst by separation to obtain the long-chain alcohol ether oxygenated additive.

Performing rapid pyrolysis under the inert atmosphere in step 1 refers to that biomass fuels are placed in a quartz tube sealed with flange covers on upper and lower sides. Vent holes are formed in the centers of the flange covers, and the vent hole in the center of the upper flange cover is a gas inlet, the vent hole in the center of the lower flange cover is a gas outlet, air in the quartz tube is exhausted with nitrogen at a rate of 0.1-0.5 L/h, then the quartz tube is filled with nitrogen at a rate of 0.1-0.5 L/h and heated, the supply of nitrogen is stopped when the temperature of the center of the quartz tube is 280-300° C., and the quartz tube is heated to 600-650° C. at a rate of 20-25° C./min. After pyrolysis is completed, the pyrolysis product is subjected to standing and has a layering phenomenon after 20-30 minutes, a brown liquid in the upper layer is a water-phase bio-oil part, a black viscous liquid in the lower layer is an oil-phase bio-oil part, and the water-phase bio-oil part is extracted from the bio-oil. Or 10% of water is added into the bio-oil, the water-phase bio-oil is soluble in water, and the oil-phase bio-oil is insoluble in water.

The biomass raw materials are agricultural and forestry wastes. The agricultural wastes include rice, corn and straw, and the forestry wastes mainly include pine and rosewood sawdust.

Application of the biomass-based long-chain alcohol ether oxygenated additive in liquid fuels is provided. The biomass-based long-chain alcohol ether oxygenated additive is added into diesel fuels and stirred at a rotation speed of 1000-1500 r/min for 20-40 minutes to obtain a biomass-based long-chain alcohol ether (TPGME)-diesel mixed fuel with improved performance. The volume ratio V % of biomass-based long-chain alcohol ether in the mixed fuel is $0\%<V\%\leq 100\%$.

Preferably, the volume ratio V % of the biomass-based long-chain alcohol ether in the mixed fuel is $20\%\leq V\%\leq 50\%$. When the volume ratio of a biomass-based long-chain alcohol ether oxygenated fuel in a short-chain ester-diesel mixed fuel is smaller than 20%, the mixed fuel can be used stably in a diesel engine, and pollutant emission can be reduced but the power output is not significantly reduced in comparison with that of diesel; when the volume ratio of the biomass-based long-chain alcohol ether oxygenated fuel is 20%-50%, the mixed fuel can be used stably in the diesel engine, and pollutant emission is significantly reduced, but the power output is significantly reduced in comparison with that of diesel; when the volume ratio of the biomass-based long-chain alcohol ether oxygenated fuel is greater than 50%, the mixed fuel can be used stably in the diesel engine with zero soot emission, but the diesel engine cannot be operated at high power.

Beneficial effects: compared with the prior art, the present invention has the following remarkable features:

1. A long-chain alcohol ether fuel prepared by pyrolysis and upgrading of bio-oil is further dehydrated and etherified on the basis of polyols to obtain a long-chain alcohol ether oxygenated fuel with a carbon chain length of $C_7$-$C_{12}$ with the oxygen content higher than 30%. Excellent combustion performance is achieved, pollutant emission is reduced, and the oxygenated fuel can be mutually soluble with diesel in any ratio, so that the use value and application prospect of a biomass-based oxygenated fuel are greatly improved;

2. A basic catalyst system can carry alkali ions on sand or a zeolite catalyst. The catalytic effect is high; a simple and practical effect is achieved; the preparation cost is low;

3. Long-chain poly-alcohol ether obtained in the present invention has excellent combustion performance and a cetane number of 60-65 which is higher than that of diesel, which can be used directly on a combustion system of an existing diesel engine without using air intake to support combustion. No modification cost is used, and meanwhile the use of petroleum resources is reduced;

4. The biomass-based long-chain alcohol ether oxygenated additive can be mutually soluble with diesel in any ratio, so that high energy consumption and a complicated mixing method are not needed. The economical efficiency is high, the operation is simple, the preparation cost is reduced, and the additive is compatible with a refueling system of current diesel refueling stations.

DETAILED DESCRIPTION OF THE EMBODIMENTS

A zeolite catalyst with K ions is used as a basic catalyst in the following embodiments, and an SAPO-34 molecular sieve catalyst is used.

A preparation process of the basic catalyst is as follows: KNO3 and a zeolite catalyst (ZSM-5, ZSM-22, SAPO and the like) are proportioned in 1.5 mmol/g; KNO3 is dissolved in water by using an equivalent-volume impregnation method and heated to 80° C.; after KNO3 is completely dissolved, the zeolite catalyst is added and stirred at a constant temperature of 80° C. for 4 hours; the mixture is dried at 120° C. and finally calcined in a muffle furnace at 550° C. for 6 hours; and after cooling to room temperature, a sample is ground to obtain the basic catalyst.

A preparation process of the SAPO-34 molecular sieve catalyst is as follows: TEAOH is used as a template, 15-40 wt % of pseudo-boehmite, 2-10 wt % of phosphoric acid, 20-40 wt % of silica sol and deionized water are used to prepare the SAPO-34 molecular sieve catalyst by using a sol-gel method.

Figure 1:
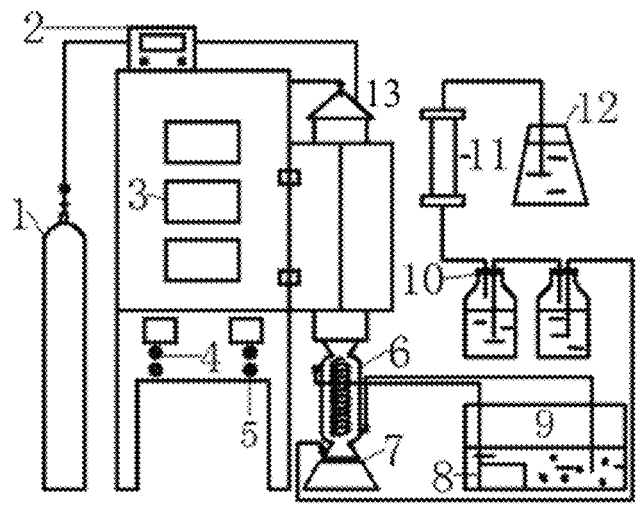
FIG. 1 is a setup diagram of a vertical pyrolysis atmosphere furnace of the present invention.

As shown in FIG. 1, pyrolysis is performed on a pyrolysis experiment setup including a nitrogen cylinder 1, a flow controller 2, a temperature display screen 3, a power switch 4, a power indicator 5, a condenser 6, a bio-oil collection cup 7, a water pump 8, a cooling pool 9, alcohol adsorption bottles 10, an activated carbon adsorption tube 11 and an aqueous solution 12. When pyrolysis is started, the power switch 4 is turned on, and then the flow controller 2 is turned on, so that nitrogen in the nitrogen cylinder 1 is introduced into a quartz tube 13 through a gas inlet in a flange; the power indicator 5 is used to measure the temperature in the quartz tube 13 during pyrolysis, and the temperature is displayed on the temperature display screen 3. A pyrolysis gas is discharged from a bottom outlet of the quartz tube 13 and enters the condenser 6; after condensation, bio-oil enters the collection cup 7; a non-condensable gas is discharged from a pyrolysis waste gas outlet; cooling water in the condenser 6 is extracted from the cooling pool 9 by using the water pump 8; and a pyrolysis waste gas discharged from the condenser 6 is adsorbed and filtered with the alcohol adsorption bottles 10, the activated carbon adsorption tube 11 and the aqueous solution 12 and then discharged into the air.

The temperature display screen 3 is used to display the heating thermal resistance temperature, the tube wall temperature, the center temperature of the quartz tube 13 in a heating section, so as to reflect the real start and end time of pyrolysis and the state of an atmosphere furnace; a cooling liquid in the condenser 6 is a mixture of ice and water at 0° C.; two openings are formed in the tail part of the condenser 6, the straight opening is used to discharge pyrolysis oil downward, and the bent opening is used to discharge the pyrolysis gas upward and prevent the pyrolysis gas from being mixed with a part of the pyrolysis oil; the alcohol absorption bottles 10 respectively contain an alcohol-water mixture with an alcohol volume ratio of 70% and an alcohol-water mixture with an alcohol volume ratio of 30%; charcoal contained in the activated carbon adsorption tube 11 is used to adsorb harmful gases in the pyrolysis gas, and the tube mouth is sealed with temperature resistant cotton; and the aqueous solution contained in a flask in the tail part is used for final adsorption treatment.

The quartz tube 13 is 86 mm in outer diameter, 80 mm in inner diameter and 1200 mm in length, the upper and lower sides are sealed with flange covers, vent holes (aperture 6 mm) are formed in the centers of the flange covers, and a temperature resistant ceramic mesh with an inner diameter smaller than 60 mm is arranged in the quartz tube 13. Since the oil production rate and pyrolysis temperature of different kinds of biomass are different, the gas pressure in the quartz tube 13 is different. Therefore, the middle hole in the upper flange cover of the quartz tube 13 is flexibly sealed with a thermocouple, and convenience is provided for discharging the gas and reducing the pressure when the pressure in the quartz tube 13 is too high.

Figure 2:
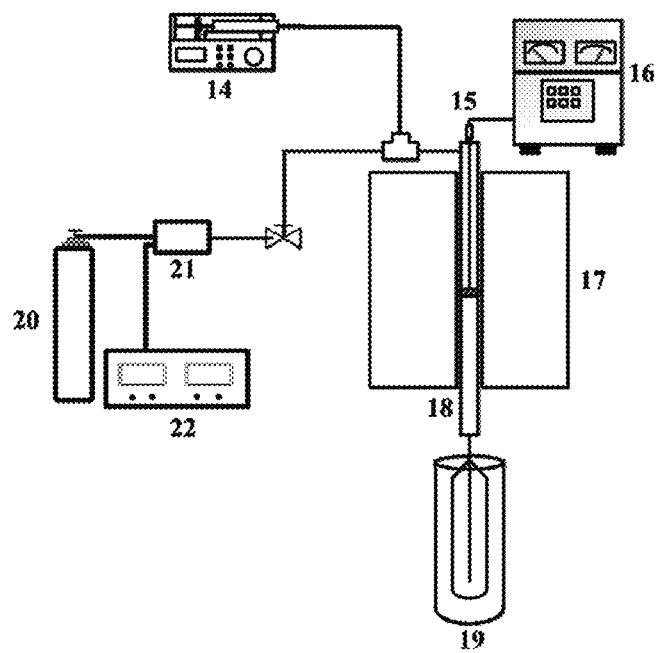
FIG. 2 is a setup diagram of a catalytic reactor of the present invention.

As shown in FIG. 2, preparation of epoxyalkane by dehydration of polyols is performed on a catalytic reaction device, and the catalytic reaction device includes a liquid injector 14, a temperature measuring thermocouple 15, a temperature controller 16, an electric heating furnace 17, a quartz catalytic reactor 18, a condenser 19, a nitrogen cylinder 20, a gas flowmeter 21 and a gas flow controller 22. First, a basic catalyst is put on a catalytic support layer of the quartz reactor 18. When a reaction starts, the nitrogen cylinder 20 is first opened, and the flow rate of nitrogen is controlled by using the gas flowmeter 21 and the gas flow controller 22, and the nitrogen serves as a carrier gas and also a reaction protective gas. A power supply is turned on, the quartz reactor 18 is heated to 400° C. by using the electric heating furnace 17, the temperature of the quartz reactor 18 is measured by using the temperature measuring thermocouple 15, and a constant temperature of 400° C. is achieved by using the temperature controller 16. After the temperature becomes constant, the polyols are injected into the quartz reactor 18 by using the liquid injector 14 and gasified into a gas after entering the quartz reactor 18, the gas passes through a catalytic layer for catalytic dehydration and then enters the condenser 19, and after the reaction is completed, epoxyalkane and water are separated to obtain the epoxyalkane.

Figure 3:
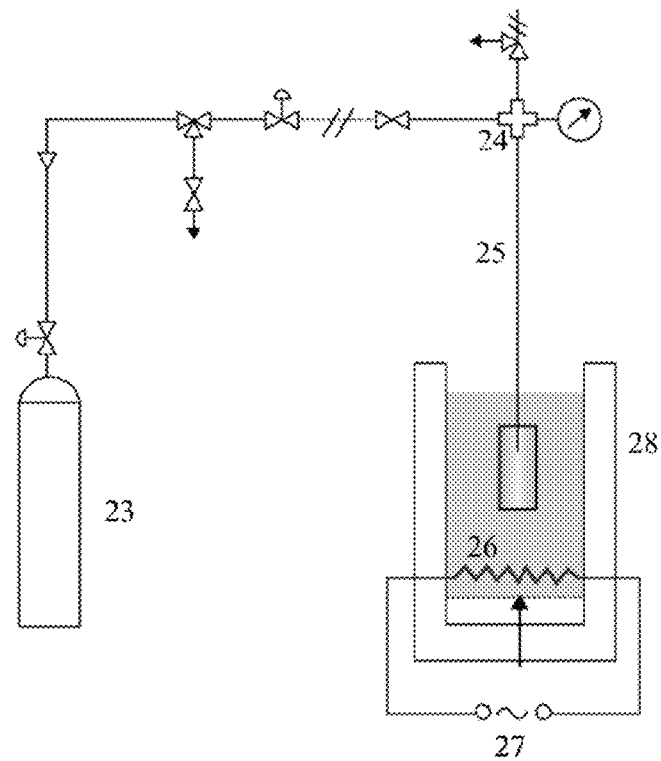
FIG. 3 is a setup diagram of a reactor of the present invention.
Figure 4:
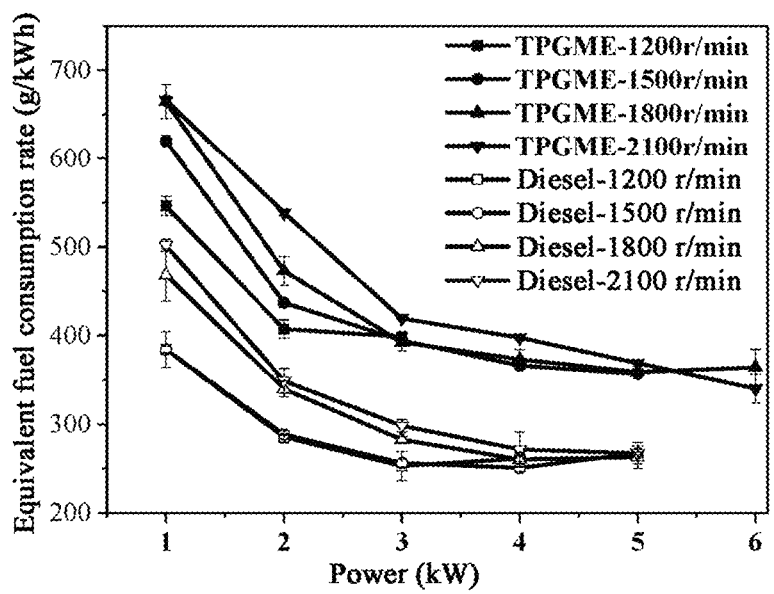
FIG. 4 shows operating characteristic curves of a TPGME-diesel mixed fuel at different rotation speeds of the present invention.
Figure 5:
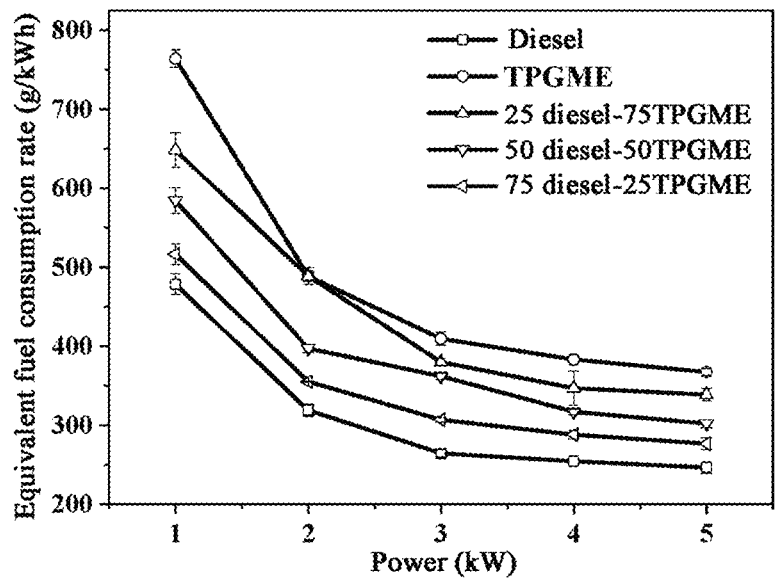
FIG. 5 shows operating characteristic curves of a TPGME-diesel mixed fuel in different mixing ratios of the present invention.

As shown in FIG. 3, catalytic hydrogenation of the water-phase bio-oil is performed in a reactor, and the reactor includes a hydrogen cylinder 23, a four-way valve 24, a magnetic stirrer 25, a heating belt 26, a power supply 27 and a reactor body 28. The water-phase bio-oil is put into the reactor body 28, an appropriate amount of a commercial catalyst HZSM-5 is added, after the reactor body 28 is closed, the hydrogen cylinder 23 is opened and communicated with the four-way valve 24, so as to introduce hydrogen into the reactor body 28. The power supply 27 is turned on, the gas-phase bio-oil in the reactor is heated by using the heating belt 26, stirring is performed by using the magnetic stirrer 25 during the reaction, the power supply 27 is turned off after the reaction is completed, the four-way valve 24 is communicated to the air to remove the gas, and after the temperature is reduced to room temperature, the polyols are obtained.

Preparation of a long-chain alcohol ether oxygenated liquid fuel by using epoxyalkane is also performed in the reactor shown in FIG. 3. Methanol and epoxyalkane are put into the reactor body 28 according to a molar ratio of 10:1, and 4 wt % of a molecular sieve catalyst is put at the same time. The reactor body 28 is closed, the hydrogen cylinder 23 is opened and communicated with the four-way valve 24, so as to introduce nitrogen into the reactor body 28 to remove air in the reactor body 28 and serves as a reaction protective gas. The power supply 27 is turned on, a liquid in the reactor 28 is heated to 65° C. by using the heating belt 26, stirring is performed by using the magnetic stirrer 25 during the reaction, the power supply 27 is turned off after the reaction is completed, the four-way valve 24 is communicated to the air to remove the gas, and after the temperature is reduced to room temperature, the long-chain alcohol ether oxygenated liquid fuel is obtained.

Embodiment 1

(1) Molded commercial biomass was purchased from the market, and straw particles with a calorific value of 3500-3800 kcal/kg were purchased in this experiment; the biomass was placed in an oven for drying at 104° C. and weighed every 5 hours until the mass of the biomass was not changed, and drying was totally carried out for 36 hours.

(2) Pyrolysis of the biomass:

In a pyrolysis stage: a temperature resistant ceramic mesh was arranged, 400 g of the straw particles were weighed and added into a quartz tube 13, a temperature measuring thermocouple was inserted into the quartz tube, and the air tightness of the quartz tube 13 was checked.

After the air tightness of the device was checked, the device was connected to an experiment table, as shown in FIG. 1. An inlet of a condenser 6 was filled with temperature resistant cotton to filter particulate matters; the outlet and inlet of an activated carbon adsorption tube 11 were filled with temperature resistant cotton; a nitrogen flowmeter was adjusted to a suitable magnitude (0.1 L/h in the experiment) when pyrolysis started; a main power supply of a pyrolysis furnace was turned on and heated; the purging time was set to be 3 minutes; the target temperature was 600° C.; the heating time was 30 minutes; and the heating rate was 20° C./min. During pyrolysis, the pyrolysis gas pressure was continuously increased with the increase of the temperature; after a pyrolysis airflow passed through the condenser 6, a liquid phase part was collected in a bio-oil collection cup 7, and a gas phase part sequentially passed through alcohol solutions 10 and the activated carbon adsorption tube 11 and was finally introduced into a water beaker to remove harmful substances in the gas.

(3) Catalytic hydrogenation and upgrading of water-phase bio-oil:

The bio-oil was subjected to standing for 1 hour, and after a viscous oil phase in the bio-oil was deposited, a light water phase in the upper layer was taken for catalytic hydrogenation and upgrading under a commercial HZSM-5 catalyst. 100 ml of water-phase bio-oil was added into a reactor body 28, and 5 g of the commercial HZ SM-5 catalyst was added; after uniform stirring, the reactor body 28 was closed, hydrogen was introduced until the hydrogen pressure was 4 MPa; the reactor was heated to 150° C., and the temperature was maintained unchanged; the reaction was performed for 3 hours; stirring was performed by using a magnetic stirrer 25 during the reaction; heating was stopped after the reaction was completed; after cooling to room temperature, hydrogen and a gas produced by the reaction in the reactor body 28 were exhausted, then the reactor body 28 was opened, a liquid and solid mixture after the reaction was poured into a beaker, a liquid and the catalyst were separated by using a centrifuge, and the upper liquid was taken to obtain polyols.

(4) Preparation of epoxyalkane by catalytic dehydration of the polyols 20 ml of the polyols were loaded into a liquid injection pump; 1 g of a basic catalyst was weighed and loaded into the quartz tube 13; a reactor was heated to 400° C., and the temperature was maintained unchanged. Nitrogen was introduced as a carrier gas with a flow rate of 100 ml/min. The polyols were injected into the quartz tube 13 at a rate of 20 ml/h, and the entire reaction time was 1 hour. The polyols entered the quartz tube 13 for gasification and then passed through a catalyst layer under the guidance of the carrier gas for a catalytic dehydration reaction. Online condensation was performed during the reaction, a reaction product was collected, and after the reaction was completed, epoxyalkane and water were separated to obtain the epoxyalkane.

(5) Preparation of a long-chain alcohol ether oxygenated liquid fuel by using epoxyalkane 100 ml of epoxyalkane and 10 ml of methanol were uniformly mixed and put into the reactor body 28, and 5 g of a molecular sieve catalyst was put at the same time; after full and uniform stirring, 0.1 MPa of nitrogen was introduced into the reactor body 28 for removing residual air in the reactor body 28 and served as a reaction protective gas; the temperature of the reactor body 28 was increased to 65° C. and kept unchanged; the power supply was turned off after the reaction was performed for 7 hours; the mixture was cooled to room temperature; and the solid catalyst was removed by centrifugal separation to obtain the target product of the present invention, namely the long-chain alcohol ether oxygenated liquid fuel.

(6) Stable combustion and reduction of pollutant emission

The collected long-chain alcohol ether oxygenated liquid fuel was mixed with diesel according to a volume ratio of 25%, 50%, 75% and 100% (power output was performed with 90% calibrated power at a calibrated speed), where a mixed fuel can be used for effectively reducing pollutant emission of an exhaust gas under the condition of stable operation of an internal combustion engine. With the increase of the mixing ratio, the emission reduction effect is improved significantly. Specific conditions are shown in FIG. 4 to FIG. 8. After the long-chain alcohol ether oxygenated liquid fuel (TPGME) is mixed with diesel, the fuel consumption rate of the mixed fuel is higher than that of diesel. However, under a high load, CO is significantly reduced, NO is slightly reduced, and soot is significantly reduced.

Straw can be replaced with rice or corn. The mass yield of the long-chain alcohol ether oxygenated additive made from straw is 19.8 wt %.

Embodiment 2

(1) Molded commercial biomass was purchased from the market, and rosewood biomass particles with a calorific value of 4300-4600 kcal/kg were purchased in this experiment; the biomass was placed in an oven for drying at 104° C. and weighed every 5 hours until the mass of the biomass was not changed, and drying was totally carried out for 24 hours.

(2) Pyrolysis of the biomass:

In a pyrolysis preparation stage: a temperature resistant ceramic mesh was arranged, 480 g of the rosewood biomass particles were weighed and added into a quartz tube 13, a temperature measuring thermocouple was inserted into the quartz tube, and the air tightness of the quartz tube 13 was checked.

Figure 6:
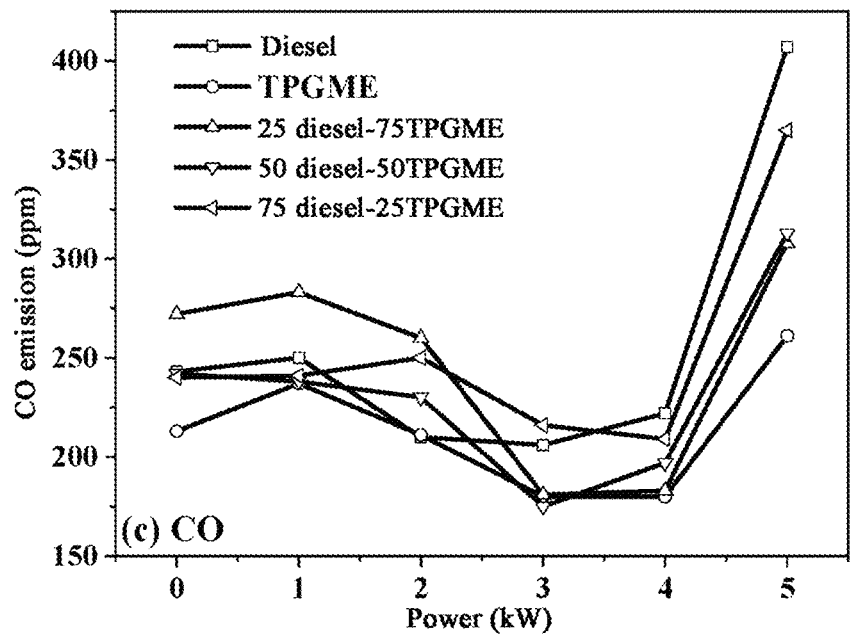
FIG. 6 shows CO emission characteristic curves of a TPGME-diesel mixed fuel in different mixing ratios of the present invention.
Figure 7:
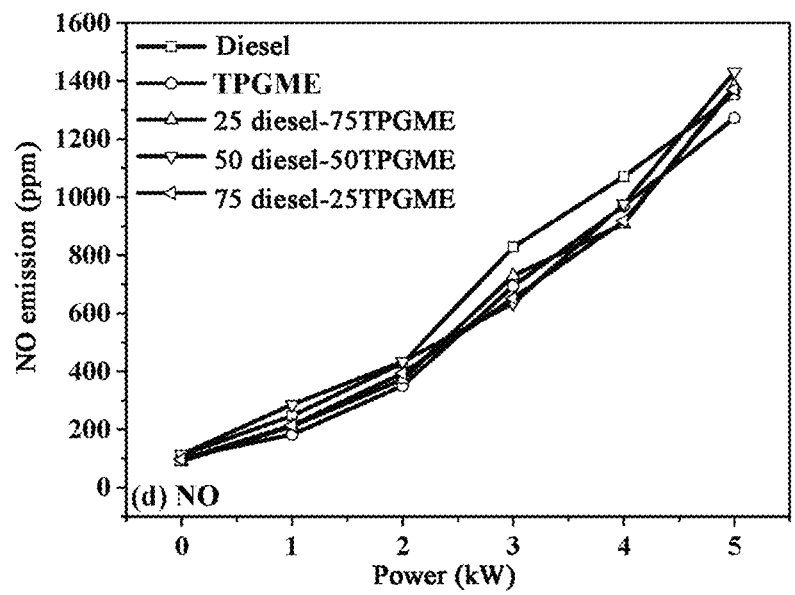
FIG. 7 shows NO emission characteristic curves of a TPGME-diesel mixed fuel in different mixing ratios of the present invention.
Figure 8:
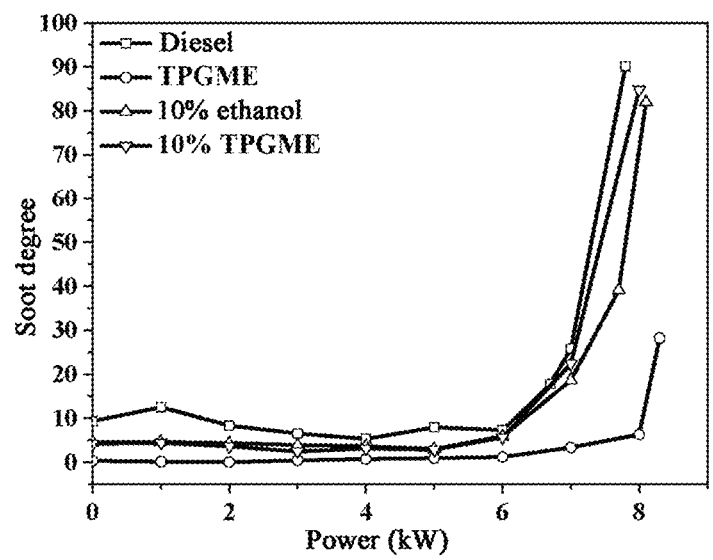
FIG. 8 shows a comparison diagram of soot emission between TPGME and diesel of the present invention.

The device was connected to an experiment table after the air tightness of the device was checked, as shown in FIG. 6. An inlet of a condenser 6 was filled with temperature resistant cotton to filter particulate matters; the outlet and inlet of an activated carbon adsorption tube 11 were filled with temperature resistant cotton; a nitrogen flowmeter was adjusted to a suitable magnitude (0.1 L/h in the experiment) when pyrolysis started; a main power supply of a pyrolysis furnace was turned on and heated; the purging time was set to be 3 minutes; the target temperature was 600° C.; the heating time was 30 minutes; and the heating rate was 20° C./min. During pyrolysis, the pyrolysis gas pressure was continuously increased with the increase of the temperature; after a pyrolysis airflow passed through the condenser 6, a liquid phase part was collected in a bio-oil collection cup 7, and a gas phase part sequentially passed through alcohol solutions 10 and the activated carbon adsorption tube 11 and was finally introduced into a water beaker to remove harmful substances in the gas.

(3) Catalytic hydrogenation and upgrading of water-phase bio-oil:

The bio-oil was subjected to standing for 1 hour, and after a viscous oil phase in the bio-oil was deposited, a light water phase in the upper layer was taken for catalytic hydrogenation and upgrading under a commercial HZSM-5 catalyst. 100 ml of water-phase bio-oil was added into a reactor body 28, and 5 g of the commercial HZSM-5 catalyst was added; after uniform stirring, the reactor body 28 was closed, hydrogen was introduced until the hydrogen pressure was 3 Mpa; the reactor body 28 was heated to 120° C., and the temperature was maintained unchanged; the reaction was performed for 2 hours; stirring was performed by using a magnetic stirrer 25 during the reaction; heating was stopped after the reaction was completed; after cooling to room temperature, hydrogen and a gas produced by the reaction in the reactor body 28 were exhausted, then the reactor body 28 was opened, a liquid and solid mixture after the reaction was poured into a beaker, a liquid and the catalyst were separated by using a centrifuge, and the upper liquid was taken to obtain polyols.

(4) Preparation of epoxyalkane by catalytic dehydration of the polyols 20 ml of the polyols were loaded into a liquid injection pump. 1 g of a basic catalyst was weighed and loaded into the quartz tube 13; a reactor was heated to 400° C., and the temperature was maintained unchanged. Nitrogen was introduced as a carrier gas with a flow rate of 100 ml/min. The polyols were injected into the quartz tube 13 at a rate of 20 ml/h, and the entire reaction time was 1 hour. The polyols entered the quartz tube 13 for gasification and then passed through a catalyst layer under the guidance of the carrier gas for a catalytic dehydration reaction. Online condensation was performed during the reaction, a reaction product was collected, and after the reaction was completed, epoxyalkane and water were separated to obtain the epoxyalkane.

(5) Preparation of a long-chain alcohol ether oxygenated liquid fuel by using epoxyalkane 100 ml of epoxyalkane and 10 ml of methanol were uniformly mixed and put into the reactor body 28, and 5 g of a molecular sieve catalyst was put at the same time; after full and uniform stirring, 0.1 MPa of nitrogen was introduced into the reactor for removing residual air in the reactor body 28 and served as a reaction protective gas; the temperature of the reactor was increased to 65° C. and kept unchanged; the power supply was turned off after the reaction was performed for 7 hours; the mixture was cooled to room temperature; and the solid catalyst was removed by centrifugal separation to obtain the target product of the present invention, namely the long-chain alcohol ether oxygenated liquid fuel.

(6) Stable combustion and reduction of pollutant emission

The collected long-chain alcohol ether oxygenated liquid fuel was mixed with diesel according to a volume ratio of 25%, 50%, 75% and 100% (power output was performed with 90% calibrated power at a calibrated speed), where a mixed fuel can be used for effectively reducing pollutant emission of an exhaust gas under the condition of stable operation of an internal combustion engine. With the increase of the mixing ratio, the emission reduction effect is improved significantly. Specific conditions are shown in FIG. 4 to FIG. 8. After the long-chain alcohol ether oxygenated liquid fuel (TPGME) is mixed with diesel, the fuel consumption rate of the mixed fuel is higher than that of diesel. However, CO is significantly reduced, NO is slightly reduced, and soot is significantly reduced under a high load. In summary, since the quality of the rosewood biomass particles is higher than that of the straw particles, the quality of the biomass-based long-chain alcohol ether oxygenated fuel obtained by using the rosewood biomass particles as raw materials is superior to that of the biomass-based long-chain alcohol ether oxygenated fuel obtained by using the straw particles as raw materials.

The mass yield of the long-chain alcohol ether oxygenated additive from rosewood is 15.1 wt %.

Embodiment 3

(1) Molded commercial biomass was purchased from the market, and rice was purchased in this experiment; the biomass was placed in an oven for drying at 100° C. and weighed every 3 hours until the mass of the biomass was not changed, and drying was totally carried out for 36 hours.

(2) Pyrolysis of the biomass:

Specifically, in a pyrolysis preparation stage: a temperature resistant ceramic mesh was arranged, 400 g of rice particles were weighed and added into a quartz tube 13, a temperature measuring thermocouple was inserted into the quartz tube, and the air tightness of the quartz tube 13 was checked.

After the air tightness of the device was checked, the device was connected to an experiment table, as shown in FIG. 1. An inlet of a condenser 6 was filled with temperature resistant cotton to filter particulate matters; the outlet and inlet of an activated carbon adsorption tube 11 were filled with temperature resistant cotton; a nitrogen flowmeter was adjusted to 0.1 L/h when pyrolysis started; nitrogen was introduced after air was totally exhausted; a main power supply of a pyrolysis furnace was turned on and heated; the purging time was set to be 3 minutes; the target temperature was 600° C.; the heating time was 30 minutes; and the heating rate was 20° C./min. During pyrolysis, the pyrolysis gas pressure was continuously increased with the increase of the temperature; after a pyrolysis airflow passed through the condenser 6, a liquid phase part was collected in a bio-oil collection cup 7, and a gas phase part sequentially passed through alcohol solutions 10 and the activated carbon adsorption tube 11 and was finally introduced into a water beaker to remove harmful substances in the gas.

(3) Catalytic hydrogenation and upgrading of water-phase bio-oil:

Specifically, the bio-oil was subjected to standing for 1 hour, and after a viscous oil phase in the bio-oil was deposited, a light water phase in the upper layer was taken for catalytic hydrogenation and upgrading under a commercial HZSM-5 catalyst. 100 ml of water-phase bio-oil was added into a reactor body 28, and 5 g of the commercial HZSM-5 catalyst was added; after uniform stirring, the reactor body 28 was closed, hydrogen was introduced until the hydrogen pressure was 3 MPa; the reactor body 28 was heated to 120° C., and the temperature was maintained unchanged; the reaction was performed for 3 hours; stirring was performed at a rate of 20 r/min by using a magnetic stirrer 25 during the reaction; heating was stopped after the reaction was completed; after cooling to room temperature, hydrogen and a gas produced by the reaction in the reactor body 28 were exhausted, then the reactor body 28 was opened. A liquid and solid mixture after the reaction was poured into a beaker. A liquid and the catalyst were separated by using a centrifuge, and the upper liquid was taken to obtain polyols.

(4) Preparation of epoxyalkane by catalytic dehydration of the polyols 20 ml of the polyols were loaded into a liquid injection pump; 1 g of a basic catalyst was weighed and loaded into the quartz tube 13; a reactor was heated to 350° C., and the temperature was maintained unchanged. Nitrogen was introduced as a carrier gas with a flow rate of 100 ml/min. The polyols were injected into the quartz tube 13 at a rate of 10 ml/h, and the entire reaction time was 1 hour. The polyols entered the quartz tube 13 for gasification and then passed through a catalyst layer under the guidance of the carrier gas for a catalytic dehydration reaction. Online condensation was performed during the reaction, a reaction product was collected, and after the reaction was completed, epoxyalkane and water were separated to obtain the epoxyalkane.

(5) Preparation of a long-chain alcohol ether oxygenated liquid fuel by using epoxyalkane 90 ml of epoxyalkane and 10 ml of methanol were uniformly mixed and put into the reactor body 28, and 5 g of a 4 wt % molecular sieve catalyst was put at the same time; after full and uniform stirring, 0.1 MPa of nitrogen was introduced into the reactor body 28 for removing residual air in the reactor body 28 and served as a reaction protective gas; the temperature of the reactor body 28 was increased to 60° C. and kept unchanged; the power supply was turned off after the reaction was performed for 12 hours; the mixture was cooled to room temperature; and the solid catalyst was removed by centrifugal separation to obtain the target product of the present invention, namely the long-chain alcohol ether oxygenated liquid fuel.

Embodiment 4

(1) Molded commercial biomass was purchased from the market, and corn was purchased in this experiment; the biomass was placed in an oven for drying at 110° C. and weighed every 6 hours until the mass of the biomass was not changed, and drying was totally carried out for 36 hours.

(2) Pyrolysis of the biomass:

Specifically, in a pyrolysis preparation stage: a temperature resistant ceramic mesh was arranged, 400 g of corn particles were weighed and added into a quartz tube 13, a temperature measuring thermocouple was inserted into the quartz tube, and the air tightness of the quartz tube 13 was checked.

After the air tightness of the device was checked, the device was connected to an experiment table, as shown in FIG. 1. An inlet of a condenser 6 was filled with temperature resistant cotton to filter particulate matters; the outlet and inlet of an activated carbon adsorption tube 11 were filled with temperature resistant cotton; a nitrogen flowmeter was adjusted to 0.5 L/h when pyrolysis started; nitrogen was introduced after air was totally exhausted; a main power supply of a pyrolysis furnace was turned on and heated; the purging time was set to be 3 minutes; the target temperature was 650° C.; the heating time was 30 minutes; and the heating rate was 25° C./min. During pyrolysis, the pyrolysis gas pressure was continuously increased with the increase of the temperature; after a pyrolysis airflow passed through the condenser 6, a liquid phase part was collected in a bio-oil collection cup 7, and a gas phase part sequentially passed through alcohol solutions 10 and the activated carbon adsorption tube 11 and was finally introduced into a water beaker to remove harmful substances in the gas.

(3) Catalytic hydrogenation and upgrading of water-phase bio-oil:

Specifically, the bio-oil was subjected to standing for 1 hour, and after a viscous oil phase in the bio-oil was deposited, a light water phase in the upper layer was taken for catalytic hydrogenation and upgrading under a commercial HZSM-5 catalyst. 100 ml of water-phase bio-oil was added into a reactor body 28, and 5 g of the commercial HZSM-5 catalyst was added; after uniform stirring, the reactor body 28 was closed, and hydrogen was introduced until the hydrogen pressure was 5 MPa; the reactor body 28 was heated to 150° C., and the temperature was maintained unchanged; the reaction was performed for 3 hours; stirring was performed at a rate of 40 r/min by using a magnetic stirrer 25 during the reaction; heating was stopped after the reaction was completed; after cooling to room temperature, hydrogen and a gas produced by the reaction in the reactor body 28 were exhausted, then the reactor body 28 was opened, a liquid and solid mixture after the reaction was poured into a beaker after the reaction, a liquid and the catalyst were separated by using a centrifuge, and the upper liquid was taken to obtain polyols.

(4) Preparation of epoxyalkane by catalytic dehydration of the polyols 20 ml of the polyols were loaded into a liquid injection pump; 1 g of a basic catalyst was weighed and loaded into the quartz tube 13; a reactor was heated to 450° C., and the temperature was maintained unchanged. Nitrogen was introduced as a carrier gas with a flow rate of 100 ml/min. The polyols were injected into the quartz tube 13 at a rate of 100 ml/h, and the entire reaction time was 1 hour. The polyols entered the quartz tube 13 for gasification and then passed through a catalyst layer under the guidance of the carrier gas for a catalytic dehydration reaction. Online condensation was performed during the reaction, a reaction product was collected, and after the reaction was completed, epoxyalkane and water were separated to obtain the epoxyalkane.

(5) Preparation of a long-chain alcohol ether oxygenated liquid fuel by using epoxyalkane 120 ml of epoxyalkane and 10 ml of methanol were uniformly mixed and put into the reactor body 28, and 5 g of a 6 wt % molecular sieve catalyst was put at the same time; after full and uniform stirring, 0.1 MPa of nitrogen was introduced into the reactor body 28 for removing residual air in the reactor body 28 and served as a reaction protective gas; the temperature of the reactor body 28 was increased to 90° C. and kept unchanged; the power supply was turned off after the reaction was performed for 6 hours; the mixture was cooled to room temperature; and the solid catalyst was removed by centrifugal separation to obtain the target product of the present invention, namely the long-chain alcohol ether oxygenated liquid fuel.

Embodiment 5

(1) Molded commercial biomass was purchased from the market, and pine was purchased in this experiment; the biomass was placed in an oven for drying at 105° C. and weighed every 4.5 hours until the mass of the biomass was not changed, and drying was totally carried out for 36 hours.

(2) Pyrolysis of the biomass:

Specifically, in a pyrolysis preparation stage: a temperature resistant ceramic mesh was arranged, 400 g of pine particles were weighed and added into a quartz tube 13, a temperature measuring thermocouple was inserted into the quartz tube, and the air tightness of the quartz tube 13 was checked.

After the air tightness of the device was checked, the device was connected to an experiment table, as shown in FIG. 1. An inlet of a condenser 6 was filled with temperature resistant cotton to filter particulate matters; the outlet and inlet of an activated carbon adsorption tube 11 were filled with temperature resistant cotton; a nitrogen flowmeter was adjusted to 0.3 L/h when pyrolysis started; nitrogen was introduced after air was totally exhausted; a main power supply of a pyrolysis furnace was turned on and heated; the purging time was set to be 3 minutes; the target temperature was 625° C.; the heating time was 30 minutes; and the heating rate was 23° C./min. During pyrolysis, the pyrolysis gas pressure was continuously increased with the increase of the temperature; after a pyrolysis airflow passed through the condenser 6, a liquid phase part was collected in a bio-oil collection cup 7, and a gas phase part sequentially passed through alcohol solutions 10 and the activated carbon adsorption tube 11 and was finally introduced into a water beaker to remove harmful substances in the gas.

(3) Catalytic hydrogenation and upgrading of water-phase bio-oil:

Specifically, the bio-oil was subjected to standing for 1 hour, and after a viscous oil phase in the bio-oil was deposited, a light water phase in the upper layer was taken for catalytic hydrogenation and upgrading under a commercial HZSM-5 catalyst. 100 ml of water-phase bio-oil was added into a reactor body 28, and 5 g of the commercial HZSM-5 catalyst was added; after uniform stirring, the reactor body 28 was closed, hydrogen was introduced until the hydrogen pressure was 4 MPa; the reactor body 28 was heated to 135° C., and the temperature was maintained unchanged; the reaction was performed for 3 hours; stirring was performed at a rate of 30 r/min by using a magnetic stirrer 25 during the reaction; heating was stopped after the reaction was completed; after cooling to room temperature, hydrogen and a gas produced by the reaction in the reactor body 28 were exhausted, then the reactor body 28 was opened, a liquid and solid mixture after the reaction was poured into a beaker, a liquid and the catalyst were separated by using a centrifuge, and the upper liquid was taken to obtain polyols.

(4) Preparation of epoxyalkane by catalytic dehydration of the polyols 20 ml of the polyols were loaded into a liquid injection pump; 1 g of a basic catalyst was weighed and loaded into the quartz tube 13; a reactor was heated to 400° C., and the temperature was maintained unchanged. Nitrogen was introduced as a carrier gas with a flow rate of 100 ml/min. The polyols were injected into the quartz tube 13 at a rate of 55 ml/h, and the entire reaction time was 1 hour. The polyols entered the quartz tube 13 for gasification and then passed through a catalyst layer under the guidance of the carrier gas for a catalytic dehydration reaction. Online condensation was performed during the reaction, a reaction product was collected, and after the reaction was completed, epoxyalkane and water were separated to obtain the epoxyalkane.

(5) Preparation of a long-chain alcohol ether oxygenated liquid fuel by using epoxyalkane 105 ml of epoxyalkane and 10 ml of methanol were uniformly mixed and put into the reactor body 28, and 5 g of a 5 wt % molecular sieve catalyst was put at the same time; after full and uniform stirring, 0.1 MPa of nitrogen was introduced into the reactor body 28 for removing residual air in the reactor body 28 and served as a reaction protective gas; the temperature of the reactor body 28 was increased to 75° C. and kept unchanged; the power supply was turned off after the reaction was performed for 9 hours; the mixture was cooled to room temperature; and the solid catalyst was removed by centrifugal separation to obtain the target product of the present invention, namely the long-chain alcohol ether oxygenated liquid fuel.

What is claimed is:

1. A preparation method of a biomass-based long-chain alcohol ether oxygenated additive, comprising the following steps:

step 1, performing a drying pretreatment on biomass raw materials at 100-110° C., performing a rapid pyrolysis on dried biomass under an inert atmosphere to obtain a pyrolysis product containing water, gases, water-phase bio-oil and oil-phase bio-oil, separating out the water-phase bio-oil, performing a catalytic hydrogenation on the water-phase bio-oil, placing the water-phase bio-oil into a first reactor, putting 10 wt % of a zeolite catalyst HZSM-5 into the first reactor for a uniform stirring to obtain a first mixture, introducing hydrogen with a pressure of 3-5 MPa, stirring the first mixture at a speed of 20-40 r/min during a first reaction at 120-150° C. for 2-2.5 hours, and after the first reaction, removing the zeolite catalyst by a first separation to obtain polyols;

step 2, performing a catalytic dehydration on the polyols obtained in step 1 under a basic catalyst system, wherein 10 wt % of a basic catalyst is weighed and loaded onto a bed layer, a second reactor made of quartz glass is heated to 350-450° C. and kept at 350-450° C., the polyols are injected into the second reactor from an upper part at a rate of 10-100 ml/h with nitrogen used as a carrier gas by using a liquid injection pump and then enter a catalyst bed layer for a catalytic reaction after a gasification, and a catalytic product is condensed to obtain epoxyalkane;

step 3, making the epoxyalkane obtained in step 2 and methanol undergo a second reaction at a constant temperature of 60-90° C. for 6-12 hours under a molecular sieve catalyst to obtain a second mixture, cooling the second mixture to room temperature, and removing the molecular sieve catalyst by a second separation to obtain the biomass-based long-chain alcohol ether oxygenated additive;

wherein, performing the rapid pyrolysis under the inert atmosphere in step 1 refers to that biomass fuels are placed in a quartz tube sealed with flange covers on upper and lower sides, wherein vent holes are formed in centers of the flange covers, a first vent hole of the vent holes in a center of an upper flange cover is a gas inlet and a second vent hole of the vent holes in a center of a lower flange cover is a gas outlet, air in the quartz tube is exhausted with nitrogen at a rate of 0.1-0.5 L/h, then the quartz tube is filled with nitrogen at a rate of 0.1-0.5 L/h and heated; a supply of nitrogen is stopped when a temperature of a center of the quartz tube is 280-300° C., and the quartz tube is heated to 600-650° C. at a rate of 20-25° C./min.

2. The preparation method of the biomass-based long-chain alcohol ether oxygenated additive according to claim 1, wherein the biomass raw materials in step 1 are dried and weighed every 3-6 hours until a mass of biomass raw materials is not changed.

3. The preparation method of the biomass-based long-chain alcohol ether oxygenated additive according to claim 1, wherein a volume ratio of the methanol to the epoxyalkane in step 3 is 9-12:1.

4. The preparation method of the biomass-based long-chain alcohol ether oxygenated additive according to claim 1, wherein a mass fraction of the molecular sieve catalyst in step 3 is 4-6 wt %.

* * * * *